(12) United States Patent
Spielberg

(10) Patent No.: US 6,398,804 B1
(45) Date of Patent: Jun. 4, 2002

(54) CORONARY ARTERY STENT WITH PORTS FOR COLLATERAL CIRCULATION

(76) Inventor: Theodore E. Spielberg, 10 Pinewood Cir., Wellesley, MA (US) 02181

( * ) Notice: Subject to any disclaimer, the term of this patent is extended or adjusted under 35 U.S.C. 154(b) by 111 days.

(21) Appl. No.: 09/634,351

(22) Filed: Aug. 9, 2000

(51) Int. Cl.[7] .................................................. A61F 2/06
(52) U.S. Cl. ..................... 623/1.14; 623/1.15; 623/1.22
(58) Field of Search ............................... 623/1.14, 1.15, 623/1.22, 1.36, 1.39, 1.4, 1.11, 1.23, 23.64; 604/7, 8; 606/158, 194, 195

(56) References Cited

U.S. PATENT DOCUMENTS 6,258,119 B1 * 7/2001 Hussein et al. ............. 606/108

* cited by examiner

Primary Examiner—Dinh X. Nguyen
Assistant Examiner—Urmi Chattopadhyay
(74) Attorney, Agent, or Firm—Ceasari and McKenna, LLP; Martin J. O'Donnell

(57) ABSTRACT

A coronary stent with one or more side ports that pierce the arterial wall to provide direct blood flow to the adjacent myocardium while simultaneously supporting the stented artery.

7 Claims, 1 Drawing Sheet

CORONARY ARTERY STENT WITH PORTS FOR COLLATERAL CIRCULATION

BACKGROUND OF THE INVENTION

1. Field of the Invention

The invention relates to coronary stents.

2. Background Information

Stents are used in physiological fluid vessels such as arteries, veins, and ducts to maintain the conduit in an open state for fluid flow through it. Typically, stents are placed in arteries that have been closed or narrowed by atheromatous plaque or clots. The stents are typically anchored in place by a variety of techniques, including sutures, barbs, and other devices. In the coronary arterial circulation they restore blood flow to the heart muscle or myocardium to preserve or restore cardiac function.

While stents restore circulation through vessels in which they are placed, and thus prevent further loss of circulatory capacity through that vessel, they do not address the problem of impaired circulation in smaller vessels for which a stent may not be suited or in the adjacent ischemic myocardium traversed by the stented coronary artery.

SUMMARY OF THE INVENTION

Accordingly, it is an object of the invention to provide an improved stent.

Further, it an object of the invention to provide a stent which can assist in restoration of circulation in vessels other than the one in which it is placed.

Still a further object of the invention is to provide a coronary stent which provides circulation to that portion of the myocardium that is adjacent to the stent.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
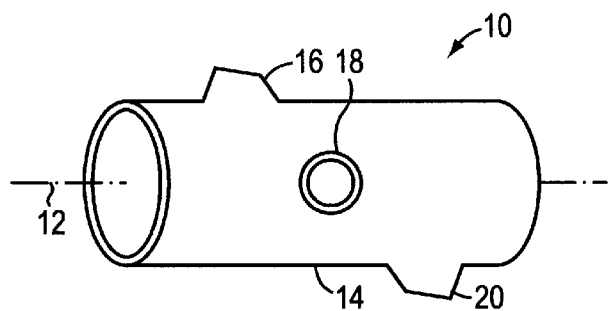
FIG. 1 is a view in perspective of a coronary stent in accordance with the present invention.
Figure 2:
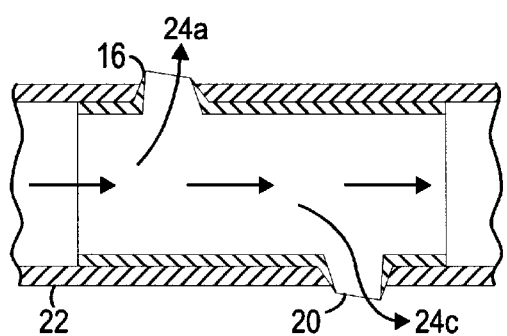
FIG. 2 is a side sectional view of the stent of FIG. 1.

In FIG. 1, a coronary stent 10 of generally tubular (e.g., cylindrical) shape has a longitudinal axis 12 along which fluid flows when the stent is placed in a blood vessel such as a coronary artery or branch thereof. The stent comprises a body 14 and a includes a plurality of hollow ports 16, 18, 20 formed around the periphery thereof and providing fluid paths of limited capacity between the interior and exterior of the stent. When the stent is inserted into one of the coronary arteries or their branches, such as artery 22 as shown in FIG. 2, the ports extend through the arterial wall and provide paths 24a, 24b, 24c for arterial blood to pass from within the stent into the surrounding environment, i.e., the myocardium. Thus, a supply of blood is provided through the ports to the myocardium adjacent to the stent in order to assist in the restoration of circulation in the cardiac tissue adjacent to the stent and, by providing this collateral circulation, prevent further damage to the heart.

Figure 1A:
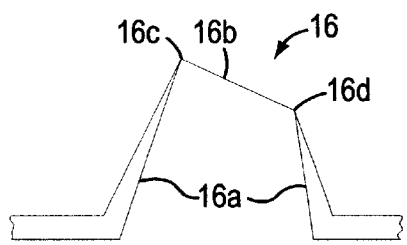
FIG. 1A is an enlarged sectional view of the port 16 of FIG. 1.

While the ports may be formed in a variety of shapes, including cylindrical, they are preferably conical in shape, as shown in more detail in FIG. 1A, and tapered in thickness from the base 16a to the tip 16b. Preferably, the tip itself is preferably slightly angled (i.e., the edge portion 16c is somewhat higher than the edge portion 16d) in order to facilitate penetration of the artery wall in a manner similar to that of a hypodermic needle. Alternatively, the tip may be rounded or otherwise smooth and the penetration of the vessel wall accomplished by a separate cutting instrument.

The ports also serve to anchor the stent in the artery in which it is implanted. To this end, there is at least one port formed on the stent, and preferably several. The number and location of the ports, as well as the size of their discharge apertures, depends on the size, condition and location of the artery in which the stent is implanted, as well as on the condition being treated. For example, where the stent is to be placed in an artery on the surface of the myocardium, the ports are desirably preferentially located on one side of the stent in order to feed blood into the myocardium from the surface. Where the stent is to be placed in an artery embedded within the myocardium, the ports may desirably be distributed circumferentially and longitudinally about the stent.

The size of the ports will also be influenced by the size and strength of the artery in which the stent is to be implanted, as well as the number of ports to be used. It is expected that a port size on the order of 10 millimeters or less will be most commonly used, but the exact size, number, and distribution of ports will be determined by the specific conditions of its application as noted above.

Figure 3:
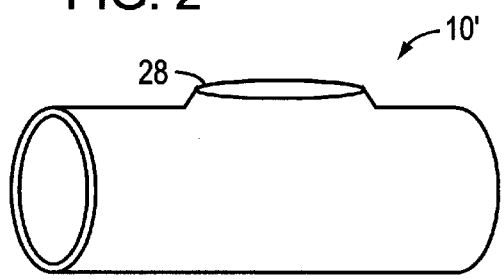
FIGS. 3 and 4 are views in perspective of further embodiments of the present invention.

As noted previously, the shape of the ports is preferably conical, as illustrated in FIGS. 1 and 2. Such shapes are readily fabricated; generally provide maximal or nearly maximal flow for a given size while minimally intruding on the structural integrity of the artery; and facilitate penetration of the arterial wall. However, other shapes may be desirable for specific conditions. For example, a cylindrical port may be used in place of a conical port. Further, an elongated port 28, i.e., a port whose length in the direction of the longitudinal axis 12 of the stent is greater than its width transverse to this axis, as shown in FIG. 3, may be used to distribute blood over a longitudinally extensive area that may have been damaged by cardiac insufficiency. Ports of differing shapes may be provided on a single stent to accommodate specific anatomical circumstances. As was shown in FIG. 1A, these ports may be tapered and angled to facilitate penetration of the arterial wall.

Figure 4A:
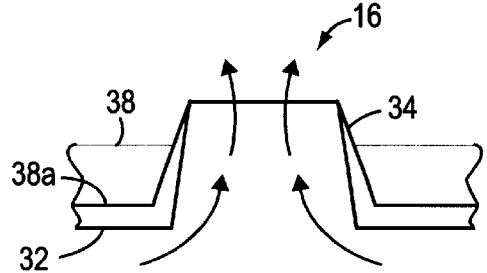
FIG. 4A is a cross sectional view along the lines A—A of FIG. 4.
Figure 4:
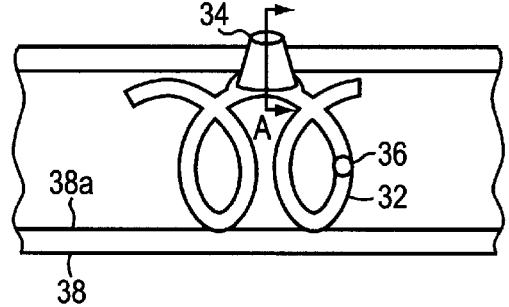

So far I have described my invention in connection with a tubular stent. The invention is not so limited, however, and may be applied to stents of different forms. FIG. 4 shows the invention as embodied in a coil-shaped stent comprising a body 32 in the form of a helical coil and a plurality of ports 34, 36 spaced along the body. As is the case with the stents of FIGS. 1–3, the stent 30 of FIG. 4 may be formed of plastic, steel, or other material, and is shown inserted in a blood vessel 38. When inserted in place, the body abuts the inner wall 38a of the vessel, while the ports 34, 36 extend through it (see, e.g., FIG. 4A) and supply blood from the interior of the artery to the environment exterior to the artery in order to promote the development and enhancement of collateral circulation. The size and number of the ports is controlled, of course, to limit the amount of fluid passing through the ports to the adjacent region.

It will be understood that the stent will find useful application not only in arteries that have been narrowed and thus need the support provided by a stent, but also in arteries that themselves have not been damaged, but that are adjacent to cardiac areas which are threatened with, or that have been damaged by, impaired circulation. In the latter case, the stent will be used solely to supply needed blood flow to the affected myocardium.

It will further be understood that the applicability of the invention is not limited to the specific illustrative stent shapes or types shown above, and that the invention may be utilized with essentially any form of coronary stent.

What is claimed is:

1. A vascular stent for insertion into the blood vessel of an animal body to improve collateral circulation in a region adjacent the stent, comprising a body for positioning within the interior of said vessel and at least one port formed on said body for penetration through the wall of said vessel to provide blood flow therethrough from the interior of said vessel into a region adjacent said port.

2. A vascular stent according to claim 1 in which said body comprises an elongated tubular vessel.

3. A vascular stent according to claim 2 in which said at least one port is generally cylindrical in shape.

4. A vascular stent according to claim 2 in which said at least one port is generally elongated in shape.

5. A vascular stent according to either claim 3 or claim 4 in which said at least one port is shaped to facilitate penetration of said vessel to enable blood flow through said port.

6. A vascular stent according to claim 2 which includes a plurality of ports disposed along said body for flow of fluid therethrough.

7. A vascular stent according to claim 1 in which said body comprises a generally helical coil.

* * * * *